United States Patent [19]

Kludas

[11] Patent Number: 5,547,997
[45] Date of Patent: Aug. 20, 1996

[54] PLANT-DERIVED COSMETIC COMPOSITION AND METHOD OF TREATMENT OF SKIN

[75] Inventor: Martin Kludas, Berlin, Germany

[73] Assignee: Chemisches Laboratorium Dr. Kurt Richter GmbH, Berlin, Germany

[21] Appl. No.: 769,411

[22] Filed: Oct. 1, 1991

[51] Int. Cl.$^6$ .......................... A61K 47/00; A61K 35/78
[52] U.S. Cl. .......................... 514/773; 514/777; 514/783; 424/195.1; 424/197.1
[58] Field of Search .................................. 514/783, 773, 514/777; 424/195.1, 197.1

[56] References Cited

U.S. PATENT DOCUMENTS

| | | | |
|---|---|---|---|
| 3,839,553 | 10/1974 | Ortega | 424/195 |
| 4,108,849 | 8/1978 | Thomas | 424/195 |
| 4,829,000 | 5/1989 | Kleinman et al. | 424/195 |
| 4,897,266 | 1/1990 | Herve et al. | 424/195 |
| 5,055,298 | 10/1991 | Kludas | 424/195 |

FOREIGN PATENT DOCUMENTS

| | | | |
|---|---|---|---|
| 62-077308 | 4/1987 | Japan | 424/195 |

OTHER PUBLICATIONS

Advertisement for Vege–Tech Hydrolyzed Wheat Protein, Mar., 1991.
Product literature from PROVITAL, S.A., relating to Proxtensol, a solution of hydrolyzed extension derived from vegetable sources.
Hood et al., 1988, "A developmentally regulated hydroxyproline–rich glycoprotein in maize pericarp cell walls," Plant Physiol. 87:138–142.
Roberts, 1990, "Structures at the plant cell surface," Curr. Op. Cell Biol. 2:920–928.
Roberts, 1989, "The plant extracellular matrix," Curr. Op. Cell Biol. 1:1020–1027.
Ye and Varner, 1991, "Tissue–specific expression of cell wall proteins in developing soybean tissues," Plant Cell 3:23–37.
Showalter and Rumeau, 1990, "Molecular biology of plant cell wall hydroxyproline–rich glycoproteins," in *Organization and Assembly of Plant and Animal Extracellular Matrix*, Academic Press, Inc., pp. 247–281.
Sharon and Lis, 1990, "Legume lectins—a large family of homologous proteins," FASEB J. 4:3198–3208.
Scripp, 1988, No. 1324, "Pierre Fabre's development of new products."Animal Pharm., 1986, No. 112, "Product introductions—U.S. launch for natural products".
Pathak et al, Journal of Investigative Dermatology, 1959, vol. 32 pp. 255 to 262.
Fowlks, Journal of Investigative Dermatology, 1959, vol. 32. pp. 249 to 254.

*Primary Examiner*—Amelia Owens
*Attorney, Agent, or Firm*—Pennie & Edmonds

[57] ABSTRACT

The invention provides compositions for the repair and remodelling of sun damaged and aged skin. The composition comprises a component of plant extracellular matrix extract in substantially native conformation, and can include a cosmetic carrier. In particular, the composition can include a glycoprotein of a plant extracellular matrix composition, a carbohydrate polymer of plant extracellular matrix composition, and mixtures thereof, each in substantially native conformation. Plant extracellular matrix extracts from Kudzu and maize are obtained.

14 Claims, No Drawings

PLANT-DERIVED COSMETIC COMPOSITION AND METHOD OF TREATMENT OF SKIN

FIELD OF THE INVENTION

This invention relates to cosmetic agents and compositions for the repair and remodeling of sun-damaged and aged skin. This invention also relates to a method for treating damaged human skin with these agents and compositions.

BACKGROUND OF THE INVENTION

Damage to the epidermal and dermal layers of the skin has been attributed to a variety of factors. Some of these factors are ultraviolet radiation and aging. Aging skin and/or skin damaged by ultraviolet radiation has characteristic ruptures and discontinuities in the dermo-epidermal interface. It is important from a cosmetic point of view to conserve an intact dermo-epidermal interface and to repair or remodel damaged dermo-epidermal interface in human skin. A damaged dermo-epidermal interface results in limited functionality and aberrations in the physiological interactions of the dermis and epidermis.

SKIN STRUCTURE

Generally stated, the skin consists of two layers that are completely different in character. The more superficial and thinner layer, the epidermis, is epithelial tissue that is derived from ectoderm. The deeper and thicker layer, the dermis, consists of connective tissue that is derived from mesoderm. These two layers are firmly cemented together to form a cohesive membrane—the skin—which varies in thickness from less than 0.5 mm to 3 or even 4 mm or more in different parts of the body. The skin rests on subcutaneous tissue which is sometimes called the hypodermis, but is not, like the epidermis, considered part of the skin. Irregularly spaced bundles of collagenic fibers extend from the dermis into the subcutaneous tissue to provide anchorage for the skin. The subcutaneous tissue permits the skin over most parts of the body to have considerable latitude of movement.

The epidermis of the skin is composed of stratified squamous keratinizing epithelium. Like all epithelium, the epidermis contains no capillaries, so it is nourished by diffusion from capillaries that are in the deeper layer of the skin, the dermis.

Since keratin is continuously worn away or shed from the surface, it must be continuously added to from beneath by the changing of living cells into keratin. This requires that the living cells of the epidermis continuously proliferate to maintain their numbers and a constant source of keratin.

Many processes are in more or less continual operation in the epidermis: (1) cell division in the deep layers; (2) cells being pushed toward the surface as a result of the underlying cell division; (3) cells farthest from the dermis being transformed into keratin; and (4) keratin desquamating from the surface. If these 4 processes are not synchronized properly—and in many skin conditions caused by age, exposure to ultraviolet radiation or disease, they are not—the character of the epidermis changes greatly.

The innermost of the inner layers is composed of basal cells that sit on the basal lamina, which separates the epidermis from the underlying dermis. All epithelial tissues have on their basal surface this continuous sheetlike extracellular structure in contact with the underlying connective tissue. In the skin, which is subject to friction, the basal lamina is anchored to the subjacent connective tissue by small fibers of collagen called anchoring fibers.

In most epithelia, fibrils of collagen (reticular fibers) complexed with amorphous protein-polysaccharides constitute another layer beneath the basal lamina called the fibrous or reticular lamina. This is a considerably thicker structure. Three constituents—basal lamina, ground substance (a highly hydrated, gel-like substance comprised of glycosaminoglycan and proteoglycan molecules), and reticular fibers—form what is called the basement membrane. The collagen of the basal lamina is primarily of type IV and that of the subjacent reticular fibers is type I and type III collagen. The thick fibers below this layer are known to be formed by collagen type I.

In this specification the term "dermoepidermal interface" is reserved for the complex structure of epidermal cell contacts, the intercellular space of epidermis, the dermoepidermal junction (basal lamina) and the papillary portion of the dermis which is structured on its interface with the epidermis.

Basal laminae, therefore, are thin layers of specialized extracellular matrix that underlie all epithelial cell sheets (and tubes). They also surround individual muscle cells, fat cells, and Schwann cells (which wrap around peripheral nerve fibers to form myelin). The basal lamina separates these cells and cell sheets from the underlying or surrounding connective tissue. However, there is increasing evidence that basal laminae serve more than simple structural and filtering roles. They seem to be able to induce cell differentiation, influence cell metabolism, organize the proteins in adjacent plasma membranes, and serve as specific "highways" for cell migration.

The basal lamina is synthesized by the cells that rest on it. Although the precise composition varies from tissue to tissue, and even from region to region within the same lamina, a major component of all basal laminae as noted above is type IV collagen. Type IV pro-alpha-chains are unusual in having extra-long extension peptides that are probably not cleaved after secretion. These procollagen molecules do not form typical collagen fibrils, although they do become covalently cross-linked to each other. In addition to proteoglycans and fibronectin, which are important constituents of basal laminae, the large glycoprotein laminin has been shown to be a major component of all basal laminae studied so far. It consists of at least two subunits (220,000 and 440,000 daltons) that are disulfide-bonded to each other. Basal laminae undoubtedly contain many other proteins yet to be identified. The detailed molecular organization of basal laminae is unknown, although there is some evidence that laminin and proteoglycan molecules are concentrated along the inner and outer surfaces of the basal lamina, with collagen molecules sandwiched in the middle. See also, Briggaman, 1982, "Biochemical Composition of the Epidermal Dermal Junction and other Dermo-epidermal interfaces," *Invest. Dermatolog,* 78(1):1–6.

Basal laminae have been shown to perform a surprising diversity of functions. The basal lamina may act as a selective cellular barrier. For example, the lamina beneath epithelial cells prevents fibroblasts in the underlying connective tissue from making contact with the epithelial cells, but it does not stop macrophages, lymphocytes, or nerve processes from passing through it. It is likely that the basal lamina plays an important part in tissue regeneration after injury. When tissues such as muscle, nerve, and epithelia are damaged, the basal lamina survives and provides a scaffolding along which regenerating cells can migrate. In this way, the original tissue architecture is readily reconstructed.

However, recent research on connective tissue has led to the conclusion that with the aging of the skin fundamental structural modifications occur, especially in the dermo-epidermal interface. These problems are of special significance to skin-care cosmetics. Since the extracellular connective tissue matrix produces an environment in which cells perform their function, the physiological interaction between cells and extracellular matrix is one of the key elements for normal epidermal-dermal interactions via an intact dermo-epidermal interface.

Beyth and Culp (1985, *Mech. Aging Devel,* 29:151) point out that the significant physical and chemical modifications observed in the aging process are a consequence of a modified extracellular matrix. Pieraggi et al. (1985, *Virch. Arch.*) found a shift of the physiological equilibrium between skin fibroblasts and the extracellular matrix in aging skin. Sengel (1985, *Development Mechanisms,* A. R. Liss, New York, pp. 123–135) points out the significance of the extracellular matrix, including the intact dermo-epidermal interface, for the transmission of morphogenetic signals. The disturbance of the normal interactions between the epidermis and the dermis in aged skin is also known from ultrastructural investigations of the dermo-epidermal interface. In addition, sunlight (ultraviolet) is known to injure the skin, not only by causing sunburn in the epidermis and inducing pigmentation, but by inducing changes in the basal membranes and deeper layers (dermis) below the epidermis. These changes appear later as premature aging of the skin—wrinkling, mottling, change in suppleness of the skin (altered connective tissue), dryness and alterations in the blood vessels. Ultraviolet radiation may also be absorbed by and damage DNA in cells present in the skin. It is further implicated in causing skin cancer.

Therefore, one may conclude that damage or injury to the dermo-epidermal interface would have serious consequences for the entire epidermal layer and could very well result in associated detrimental cosmetic implications.

Research in the fields of cell biology and embryology has also shown that an extracellular connective tissue matrix consisting of genetically distinct collagen types, proteoglycans and structural glycoproteins has a significant influence on cell proliferation, mitogenesis and morphogenesis (Hay, 1983, *Mod. Cell. Biol.* 2:509; Bernfield et al., 1984 in *The Role of Extracellular Matrix in Development,* A. R. Liss, New York). It has been postulated that there exists a "dynamic reciprocity" between the extracellular matrix on the one hand, and the cytoskeleton and the nuclear matrix on the other hand. The extracellular matrix is thought to exert physical and chemical influences on the geometry and the biochemistry of the cell via transmembrane receptors so as to alter the pattern of gene expression by changing the association of the cytoskeleton with the mRNA, and the interaction of the chromatin with the nuclear matrix (Bissell et al., 1982, *J. Theor. Biol.* 99:31–68).

2.2. PLANT EXTRACELLULAR MATRIX

Most animal cells (apart from blood cells) are in contact with an intricate meshwork of interconnecting, interacting extracellular macromolecules that constitute the animal extracellular matrix. Until recently, the vertebrate extracellular matrix was thought to serve mainly as a relatively inert scaffolding that stabilized the physical structure of tissues. It is now clear that the matrix plays a far more active role in regulating the behavior of cells that contact it—influencing their development, migration, proliferation, shape and metabolic function (see Hay, 1983, *"Cell and Extracellular Matrix,* "Mod Cell Biol 2:509–548; and Kleinman et al., 1981, "Role of Collagenous Matrices in the Adhesion and Growth of Cells," *Cell Biol.* 88(3):473–486).

The plant extracellular matrix, or "cell wall" as it is commonly called, is a similarly constructed multilayered network. Like the animal extracellular matrix, the plant extracellular matrix provides a dynamic support, regulating cell behavior via the connections with the plasma membrane (see Roberts, 1989, *Curr. Op. Cell Biol.* 1:1020–1027).

Plant extracellular matrix is a complex mixture of polymers, which are present in varying amounts depending on the plant species. The extracellular matrix composition varies within an individual plant as well, depending on its location (Roberts, 1990, *Curt. Op. Cell Biol.* 2:920–928). Plant cell walls have traditionally been divided into primary cell walls that accommodate cell expansion and secondary cell walls that are fully elaborated around expanded cells. Although the relative amounts may vary, the following components are usually present in primary cell wall of higher plants: pectin, xyloglycan, protein, arabinoxylan, $\beta$1–3 and $\beta$1–4 glucans, cellulose, callose, and lignin (see Roberts, 1989, Supra). Grasses (graminaceous monocots) characteristically have low levels of pectin, xyloglycan and protein, and very high levels of arabinoxylan and the glucans (Roberts, 1989, supra).

A number of proteins have been characterized from plant extracellular matrix. Much attention has focused on the hydroxyproline-rich glycoproteins. More recently discovered proteins include repetitive proline-rich proteins, arabinogalactan proteins, extensins, solanaceous lectins, glycine-rich proteins, and thionins (Roberts, 1990, supra). Attachment proteins, analogous to animal integrins, perhaps even containing the fibronectin RGD cell attachment consensus sequence, are also likely present in plant extracellular matrix (see Roberts, 1989, supra).

COSMETIC SKIN TREATMENT

In cosmetic skin preparations, individual active substances or combinations of isolated individual components of the extracellular matrix are often used in the hope of preventing skin aging by substitution of deficient or damaged skin components.

For instance, skin preparations are disclosed in the German Patent DE-PS 20 64 604. This reference speaks of increasing the soluble, i.e., not cross-linked portion of the collagen in the skin, by using native soluble collagen (tropocollagen) to improve the age-dependent ratio of soluble to insoluble collagen in favor of the soluble fraction, and to slow down the loss of elasticity of the skin.

A cosmetic preparation containing collagen of the dermo-epidermal interface is also disclosed in German Patent DE-PS 30 46 133. In contrast to the use of the interstitial collagen types I, II and III which are structurally similar to each other, the use of the dermo-epidermal interface collagen (collagen type IV) is therein claimed to have a higher effectiveness, since said dermo-epidermal interface collagen is adopted better by the cells. The stated object of using dermo-epidermal interface collagen was to promote regeneration and faster growth of new skin cells. Thus the cosmetic preparation tries to counteract a feature of skin aging by supplying an individual substance.

U.S. Pat. No. 4,451,397 discloses the use of collagen in connection with mucopolysaccharides for cosmetic purposes. The main subject matter of the invention disclosed in this patent is a method for producing a solution or a homogeneous gel composition consisting of the aforementioned substances, and the use of these substances in a cosmetic preparation to improve skin tone.

Other references additionally disclose the use of connective tissue components for skin treatment. U.S. Pat. No. 3,991,184 to Kludas discloses the use of untreated, soluble collagen having an unchanged substantially non-cross-linked structure for use in treating the skin. U.S. Pat. No. 4,327,078 to Charlet et al. discloses cosmetic agents containing, as an active ingredient, soluble elastin for treatment of aging skin. In addition, U.S. Pat. No. 4,464,362 discloses cosmetic compositions containing inactive cultures of bacteria of the genus *Bifidobacterium* or bacteria related to this genus for promoting DNA repair in skin cells.

However, cosmetic compositions based on components from animals present serious problems in the form of the potential for transmission of pathogens, in particular viruses and viral-like infectious agents. In that regard, the recent outbreak of bovine spongeform encephalopathy (BSE) in Europe, concentrated primarily in Great Britain, causes great concern, since transmission of the infectious agent through bovine products cannot be excluded. Thus, the art looks to other sources of components for cosmetic compositions.

Hydrolyzed vegetable proteins have attracted attention. Two prominent commercial products are hydrolyzed wheat protein (Vege-Tech, Glendale Calif.) and hydrolyzed extensin (hydroxyproline-containing glycoprotein) derived from plants (Provital, S. A.). Thomas (U.S. Pat. No. 4,108,849, Aug. 22, 1978) describes alkaline extraction and sterilization, especially autoclaving, of, inter alia, plant tissues or cells for medical and cosmetic purposes.

Therefore, it is an object of the present invention to counteract inadequate cell-matrix interaction, due to aging and ultraviolet light exposure, to repair or remodel the damaged skin which is characterized by damaged dermo-epidermal interface, and to enable normal interactions of epidermis and dermis.

SUMMARY OF THE INVENTION

The present invention provides a composition comprising a component of plant extracellular matrix extract in substantially native conformation. The plant extracellular matrix extract can further comprise a glycoprotein of a plant extracellular matrix extract in substantially native conformation, a carbohydrate polymer of a plant extracellular matrix extract in substantially native conformation, and mixtures thereof. The composition can also comprise a cosmetic carrier.

The present invention further provides a method of treating aged or damaged skin, comprising applying a composition comprising a component of plant extracellular matrix extract to the skin. The component of plant extracellular matrix extract for use in the method of treating skin is in substantially native conformation.

DETAILED DESCRIPTION OF THE INVENTION

The present invention provides a plant-derived cosmetic composition comprising a component of plant extracellular matrix extract in substantially native conformation. Such a component is any molecule that is found in plant extracellular matrix, e.g., a polymer such as a protein, a glycoprotein, a carbohydrate, a proteoglycan, or a mucopolysaccharide. In a preferred embodiment, the composition comprises a glycoprotein of a plant extracellular matrix extract in substantially native conformation. Non-limiting examples of a glycoprotein include a hydroxyproline-rich protein, a repetitive proline-rich protein, an arabinogalactan protein, a lectin, and mixtures thereof. In yet a further embodiment, the composition comprises a carbohydrate polymer of a plant extracellular matrix extract in substantially native conformation. Non-limiting examples of carbohydrate polymers are pectin, xyloglycan, arabinoglycan, glucan, callose, lignin, and mixtures thereof. In yet another embodiment, the composition comprises such a glycoprotein and such a carbohydrate polymer.

As described in section 4.2, infra, the ratio of the several plant extracellular matrix components can vary, depending on the source of the plant extracellular matrix, i.e., what type of plant is used and how the components are obtained.

As used herein, the phrase "plant extracellular matrix extract" indicates that a component normally found in association with plant extracellular matrix lacks the interactions—covalent or otherwise—normally associating the component with the plant extracellular matrix. In one embodiment, the component of the plant extracellular matrix extract is extracted from plant tissue, which contains the extracellular matrix, thereby releasing the component from the interactions associating it with the extracellular matrix. However, the compositions of the subject invention are not limited by the method the components are made. For example, rather than extracting the component from plant extracellular matrix, the component can be produced by a suspension of plant cells in vitro, produced by recombinant techniques, or synthesized chemically. Components produced in vitro are utilized free of the plant cells in suspension. Although as found in nature a component of plant extracellular matrix is theoretically soluble, i.e., if found as a monomer it would go into aqueous solution, because the component is naturally associated with the extracellular matrix, it is not found in solution.

As used herein, the term "substantially native conformation" means that the component of plant extracellular matrix extract is expected to be found in substantially the same structural and three dimensional form that it had in the plant extracellular matrix, i.e., the component retains or substantially retains its structure and secondary and tertiary conformation. Only the quaternary conformation, i.e., the interactions with other molecules, is absent. Thus, the extracted component of the plant matrix extract retains a biologically active conformation. A biologically active conformation is one that allows for normal interactions with cells or other extracellular matrix components, or both, i.e., allows the normal functions of the component to proceed.

Although the present invention is not limited by any theory or mechanism, it is believed that the preservation of substantially native conformation of an extracellular matrix component is essential for repair of damaged skin. Cosmetics that lack functionally active extracellular matrix components cannot be expected to mediate cell attachment, cell signalling and activation, and matrix functions necessary for regeneration of a healthy dermo-epidermal interface. By providing plant extracellular matrix components in substantially native conformation, as defined herein, the cosmetic compositions and methods of the present invention provide functionally active extracellular matrix components capable of mediating cell attachment and repair of damaged dermo-epidermal interface.

The underlying problem addressed by the present invention has been the inability, to date, to provide a plant-derived composition or treatment that would enable the conservation and/or repair and remodeling of a dermo-epidermal interface damaged by factors such as aging or exposure to environmental factors such as ultraviolet light. This invention, therefore, relates to cosmetic compositions and methods for their use which, utilizing appropriate therapy, maintain an intact dermo-epidermal interface and are effective in repairing and remodeling a damaged dermo-epidermal interface. More specifically, the cosmetic compositions utilized in this invention provide components of the plant extracellular matrix in their natural or native, unaltered structural form, which repair damaged dermo-epidermal interface of skin. The result of treatment with a component of plant extracellular matrix extract is an enhanced and healthy skin wherein the normal physiological functioning and interactions between the various layers of the skin have been restored.

PLANT SOURCES

All plants have extracellular matrix and thus any type of plant can be utilized to provide a source of raw material for extraction and then utilized in the cosmetic compositions of the present invention. However, certain types of plants are preferred because they are easier to cultivate and harvest, easier to extract, and may yield more of a preferred active agent—hydroxyproline-rich protein. Plants for use in the present invention include but are not limited to seaweeds, grasses, food crop plants, ornamental plants and weeds. In particular embodiments, infra, kudzu leaves and maize provide a suitable extract. Other particular sources of plant extracellular matrix include kelp, carrot, tomato, tobacco, bean, soybean, sugar beet, potato, melon and petunia. The extract can be obtained from leaves, stems, roots, fruit and tuber (see, e.g., Showalter and Rumeau, 1990, in *Organization and Assembly of Plant Extracellular Matrix*, Academic Press, pp. 247–281).

As is known in the art, both primary (i.e., growing) and secondary (i.e., grown) plant cell wall (i.e., extracellular matrix) contain extracellular matrix components for use in the invention. However, because primary cell wall is more "fluid" and contains fewer cross-links to allow for cell growth, less plant tissue can be used to prepare extracellular matrix extract from primary cell wall.

PLANT EXTRACELLULAR MATRIX EXTRACT

Any method known in the art for the preparation of a component of plant extracellular matrix in solubilized form, including well known techniques of expressing recombinant DNA (see, e.g., Showalter and Rumeau, 1990, in *Organization and Assembly of Plant Extracellular Matrix*, Academic Press, pp. 247–281), or chemical synthesis, can be used to obtain plant extracellular matrix extract. In another embodiment, components can be obtained from growth medium of plant cells in suspended culture (see Bacic et al., 1988 in *The Biochemistry of Plants, Volume* 14, Stump and Conn (eds.), Academic Press, pp. 297–371).

In a preferred embodiment, plant tissue is extracted. Plant tissues are minced, and washed in a solution designed to minimize degradation due to injury. Preferably, the wash solution contains a suitable antioxidant at a concentration sufficient to inhibit oxidation, thereby reducing the oxidation of phenols and pigments and prevent browning. The wash solution also preferably contains a peroxide scavenger or inhibitor of peroxide release, since injured plant tissues release hydrogen peroxide. In a particular embodiment, the anti-oxidant and peroxide release inhibitor are sodium metabusulfite ($Na_2S_2O_5$), present in a concentration necessary to inhibit oxidation and peroxide release. In an Example, infra, $Na_2S_2O_5$ is present at a concentration of 4 mM, although any concentration in the mM range is suitable.

Preferably, the wash solution also contains a preservative, for example, Phenonip at a concentration of about 0.3%. However, any acceptable preservative can be used.

The minced plant tissues are washed extensively to remove impurities and low molecular weight components. In a particular embodiment, the tissues are washed in three changes of wash buffer for about 24 hours each. Preferably the minced plant tissue are constantly and vigorously agitated during the washing steps. Preferably, the washing is done in a cold room, i.e., about 4° C. The ratio of plant tissue to wash solution should be about 1 to 10 (weight to volume), but can range from about 1:3 to about 1:20 (w/v), or within any suitable parameters known to one of ordinary skill. For example, the plant tissue can be washed in more than three changes of wash solution, using less than about a 1:10 ratio of tissue to solution (w/v) in each step. Preferably, as much wash solution as possible is removed after each washing step. In a particular embodiment, the minced tissue is compressed under pressure to remove solution.

After washing with washing solution containing antioxidant or anti-peroxide, or both, the plant tissue is washed with the same volume of water, preferably containing a preservative, e.g., Phenonip (0.3%). As much water as possible is removed, e.g., by compression under pressure.

After washing, plant extracellular matrix components for use in the cosmetic compositions are solubilized and extracted from the plant tissue under conditions that preserve the native, biologically functional structure and conformation of the plant extracellular matrix components. Any extraction technique that preserves the functionally active structure of these components may be used; in a particular embodiment, a high concentration salt solution designed to liberate the individual macromolecular components of the tissues may be used. Preferably, the extraction solution contains a preservative, for example, Phenonip at 0.3%.

Salt solutions at moderately low pH are preferred to extract the native molecules into solution, and to avoid degrading the polymers by hydrolysis. In a preferred embodiment, an extraction solution comprising calcium chloride ($CaCl_2$) at a concentration of 0.2 to 1.0M is used. In another embodiment, guanidine-HCl at a concentration of 0.5 to 2.0M is used. In yet a further embodiment, both $CaCl_2$ (0.2 to 1.0M) and guanidine-HCl (0.5 to 2.0M) are used. The relative amounts of plant extracellular matrix components that are extracted depends in part on the type of extraction solution used.

In a particular embodiment, the plant tissue may be treated in a limited way with a proteolytic enzyme, in order to cleave cross-links or cross-linked portions of macromolecules sought for extraction. In particular embodiments pepsin, preferably at a temperature from about 4° to about 18° C. (Miller et al., 1972, *Biochem* 11:4903), or trypsin is used.

The minced, washed plant tissue is extracted with extraction solution preferably but non-limiting in a ratio of about 1:10 (w/v) plant tissue to extraction solution. The ratio may be adjusted depending on the type of plant, the extraction solution used, and whether primary or secondary plant cell wall will be extracted. For example, more solvent may be used with primary tissue (or less with secondary tissue) because more component will be extracted. Preferably, the plant tissues are constantly and vigorously agitated during the extraction period. Extraction continues for about at least 24 hours.

Insoluble material is removed from the extract, for example by compression, and the extract is filtered. In a particular embodiment, a 0.45 μl filter is used.

The plant extracellular matrix composition obtained according to the invention comprises one or more of the following in substantially native conformation: glycoproteins, including hydroxyproline-rich proteins (extensins); repetitive proline-rich proteins, arabinogelactan proteins, and lactins; and carbohydrate polymers such as pectin, xyloglycan, arabinoglycan, glucan, callose and lignin.

The relative proportion of these plant extracellular matrix components in the extract depends upon the source of the extract, i.e., the type of plant used and on the extraction technique employed. For example, an extract of Kudzu leaves contains more hydroxyproline-rich glycoproteins than an extract from maize. However, in each case the components of extracellular matrix have substantially native conformation and are capable of mediating the biological function of the extracellular matrix, and thus are useful for cosmetic compositions.

Extraction and purification of hydroxyproline-rich protein is also described by Hood et al., 1988, *Plant Physiol.* 87:138–142. Purification of the components of plant extracellular matrix extract is well known in the art.

TREATMENT OF SKIN CONDITIONS

The component of plant extracellular matrix extract as disclosed herein can be mixed with an acceptable cosmetic carrier to form a cosmetic composition, which can be topically applied to skin. Typical cosmetic carriers for use in the invention include but are not limited to those agents described in Section 4.4, infra.

The cosmetic composition can be applied to the skin in biologically or therapeutically effective amounts over a period of time sufficient to result in repair or remodeling of the dermo-epidermal interface. This repair or remodeling will typically be apparent from a visible improvement of the appearance of the outside of the skin.

While not intending to be bound by any theory or mechanism, it is believed that since there is such a strong and irrefutable interrelationship between the dermo-epidermal interface and the other layers of the skin in the dermis and epidermis, and that plant extracellular matrix components can mediate cell functions, i.e., via transmembrane proteins and cytoskeletal components, a positive repairing and remodeling effect in the dermo-epidermal interface will lead to a reestablishment of normal and healthy interactions with and between these other skin layers. It is this reestablishment in part that contributes the overall improvement in the health and appearance of the skin.

The particular amount of cosmetic composition to be applied to the skin and the duration or number of applications can be determined easily on an individual basis by utilizing the cosmetic composition until a visible improvement of the outer surface of the skin results. One skilled in the art of dermatological medicine or cosmetology and who is familiar with standard topical treatment means would also be in a position to easily evaluate a beneficial course of treatment. Examples of typical and preferable treatments would be application two or three times a day with a cosmetic composition containing about 10% of the plant extracellular matrix extract by volume. The percentage of plant extracellular matrix extract present in the cosmetic composition can vary, of course, depending upon the cosmetic carrier and the severity of the skin condition to be treated, however, the plant extracellular matrix extract comprises not less than about 0.1%, and as much as 99%, by volume, of the cosmetic composition. In the most severe cases, plant extracellular matrix extract exclusively can be utilized directly or topically without the cosmetic carrier.

EXAMPLE: COSMETIC FORMULATIONS

The term "cosmetic" or "cosmetic composition," as used herein is intended to include all types of products that are applied in any manner directly to the skin and including but not limited to, in addition to a component of plant extracellular matrix extract as disclosed herein, conventional ingredients such as lanolin, beeswax, oleic acid, spermaceti, almond oil, castor oil, tragacanth gum, clay, magnesia, talc, itetal stearates, chalk, magnesium carbonate, zinc stearate, kaolin, etc.

Said compositions may take the form of fatty or non fatty creams, milky suspensions or emulsions of the water-in-oil or oil-in-water types, lotions, gels or jellies, colloidal or non colloidal aqueous or oily solutions, pastes, soaps, aerosols, soluble tablets (to be dissolved in a fluid, such as water) or sticks.

The amount of active ingredient contained in cosmetic compositions according to the invention applied to the skin may vary between wide limits, depending upon the formulation and the frequency of use of said compositions. Generally, said compositions contain from 0.1%–99% by weight of the plant extracellular matrix extract.

The cosmetic compositions used in the method according to the invention can also contain conventional vehicles or carriers, such as solvents, fats, oils and mineral waxes, fatty acids and derivatives thereof, alcohols and derivatives thereof, glycols and derivatives thereof, glycerol and derivatives thereof, sorbitol and derivatives thereof, surface-active agents of the anionic, cationic or nonionic type, emulsifying agents, preserving agents, perfumes, etc.

A few examples of cosmetic compositions used in methods according to this invention are given hereafter. In said examples, the percentages are by weight. In addition, the cosmetic composition according to the present invention can be produced and used in the same manner as in conventional cosmetics.

The following formulations are exemplary embodiments of the invention, but are not intended to limit the scope of this invention or restrict it to these particular formulations:

CREAM

A cream (oil-in-water) containing the active composition (plant extracellular matrix extract prepared according to the present invention) comprising:

| | | |
|---|---|---|
| a) | glycerol monostearate | 12.0% |
| | cetyl stearyl alcohol ethylene oxide adduct containing about 12 mole ethylene oxide | 1.5% |
| | cetyl stearyl alcohol ethylene oxide adduct containing about 20 mole ethylene oxide | 1.5% |
| | cetyl alcohol | 2.0% |
| | 2-octyl-dodecanol | 10.0% |
| | isoctyl stearate | 8.0% |
| | caprylic/capric acid triglyceride | 3.0% |

|    |                                                                                                  |        |
|----|--------------------------------------------------------------------------------------------------|--------|
|    | methylparaben                                                                                    | 0.17%  |
|    | propylparaben                                                                                    | 0.03%  |
|    | and                                                                                              |        |
| b) | water, distilled                                                                                 | 46.8%  |
|    | glycerol                                                                                         | 5.0%   |
|    | and                                                                                              |        |
| c) | plant extracellular matrix extract according to the present invention (prepared as explained above) | 10.0%  |

Mixture a) is heated to approximately 70° C. and mixture b) is likewise heated to approximately 70° C. and then added while stirring to mixture a).

Stirring is continued until the cream has cooled down to approximately 30° C. Then composition c) is added while stirring and the cream is homogenized.

By the term cream used herein are meant all cosmetic materials which include, for instance, hand creams, cleansing creams, milky lotions, cold creams, vanishing creams, hair creams, foundation creams, beauty washes, facial packs and the like.

EMULSION

Oil-in-water emulsion (o/w) containing the active composition (the plant extracellular matrix extract prepared according to the present invention) comprising:

|    |                                                                                                  |        |
|----|--------------------------------------------------------------------------------------------------|--------|
| a) | glycerol monostearate                                                                            | 3.0%   |
|    | cetyl stearyl alcohol                                                                            | 2.0%   |
|    | cetyl stearyl alcohol ethylene oxide adduct containing about 12 mole ethylene oxide              | 1.5%   |
|    | cetyl stearyl alcohol ethylene oxide/adduct containing about 20 mole ethylene oxide              | 1.5%   |
|    | glycerol monooleate                                                                              | 0.5%   |
|    | 2-octyl-dodecanol                                                                                | 10.0%  |
|    | methylparaben                                                                                    | 0.17%  |
|    | propylparaben                                                                                    | 0.03%  |
|    | and                                                                                              |        |
| b) | water, distilled                                                                                 | 66.3%  |
|    | glycerol                                                                                         | 5.0%   |
|    | and                                                                                              |        |
| c) | plant extracellular matrix extract according to the present invention                            | 10.0%  |

Mixture a) is heated to approximately 70° C. and mixture b) is likewise heated to approximately 70° C. and added while stirring to mixture a).

Stirring is continued until the o/w emulsion has cooled down to approximately 30° C. Then composition c) is added while stirring and the o/w emulsion is homogenized.

GEL

A gel containing the active composition (plant extracellular matrix extract prepared according to the present invention) comprising:

|    |                                                                       |         |
|----|-----------------------------------------------------------------------|---------|
| a) | water, distilled                                                      | 65.10%  |
|    | polyacrylic acid (type carbopol 940)                                  | 0.80%   |
|    | methylparaben                                                         | 0.17%   |
|    | propylparaben                                                         | 0.03%   |
|    | and                                                                   |         |
| b) | polyoxyethylene (20) sorbitan trioleate                               | 0.30%   |
|    | sorbitan monooleate                                                   | 0.15%   |
|    | caprylic/capric acid triglyceride                                     | 2.50%   |
|    | and                                                                   |         |
| c) | water, distilled                                                      | 20.15%  |
|    | triethanolamine                                                       | 0.80%   |
|    | and                                                                   |         |
| d) | plant extracellular matrix extract according to the present invention | 10.0%   |

Preparation of the gel is carried out as follows:

For obtaining a), polyacrylic acid is dispersed under rapid stirring in water; then the components of b) are mixed and added under stirring to a); likewise the aqueous triethanolamine solution c) is added under stirring; finally composition d) is added under stirring.

The preparations of cosmetic agents of the invention and the effectiveness of such a cosmetic agent are demonstrated in the Examples which follow.

EXAMPLE: EXTRACTION FROM KUDZU

Two hundred gm of dried leaves were minced and washed in 3 l of 4 mM $Na_2S_2O_5$ (sodium metabisuflite) containing 0.3% Phenonip as preservative. The minced tissue was constantly and vigorously agitated during three (3) washes of about 24 hrs each and kept in a cold room for the entire procedure. The leaves were compressed under pressure after each wash to remove as much wash solution as possible. Sodium metabisulfite was used in this case as an antioxidant to reduce oxidation of phenols and plant pigments which would lead to browning. Sodium metabisulfite also inhibits the release of hydrogen peroxide, which occurs when plant tissues are injured. After the three washing steps, the leaves were washed with the same amount of water containing 0.3% Phenonip to remove the sodium metabisulfite.

Subsequently, the residue containing the minced leaves was extracted with 3 l of 0.2M $CaCl_2$ for at least 24 hrs. Again the tissues were constantly agitated during the extraction period. Finally, the insoluble material was removed by filter compression and the extract filtered through a 0.45 μ (Millipore HVLP 14250) filter.

The extracellular matrix extract collected from the Kudzu tissue contained native plant proteins, including the hydroxyproline-rich plant protein extensin and other glycoproteins, as well as carbohydrate polymers (pectins). The molecular weights of these components range in the scaling of several hundred thousand daltons, accompanied by smaller molecular weight submits.

EXAMPLE: EXTRACTION FROM MAIZE

Two hundred gm of maize were minced and washed in 1.5 l of 4 Mm $Na_2S_2O_5$ containing 0.3% Phenonip preservative. The minced tissue was washed three times with wash solution, and once with water containing 0.3% Phenonip, as described in Section 5, supra. The residue was extracted with 2.0 l of 0.2M $CaCl_2$ for 24 hours. The insoluble material was removed by filter compression and the extract was filtered on a 0.45 μ filter (Millipore HVLP 14250).

The maize extract contained 0.08% protein as determined by the Lowry method (Sigma Chemical Co.). The hydroxyproline concentration was 12 μg/ml.

EXAMPLE: A CLINICAL TEST

Marked areas of the dorsal (back of hand) skin of volunteers having clinical signs of aging skin are treated with the following test creams for four weeks, twice a day:

a) cream (oil-in-water) having 10% of the active composition (plant extracellular matrix extract prepared according to the present invention);

b) cream base (oil-in-water) as control.

The skin is evaluated for improvement in luminosity, moisturization, satinity and elasticity, and reduction of visible signs of aging and of the depth of wrinkles and fine lines.

This experiment can show and establish that the topical application of the agent of the present invention results in improved luminosity, moisturization, satinity and elasticity of the skin. Visible signs of aging are reduced and the depth of the wrinkles and fine lines is reduced.

The present invention is not to be limited in scope by the specific embodiments described herein since such embodiments are intended as but single illustrations of one aspect of the invention. Indeed, various modifications of the invention in addition to those shown and described herein will become apparent to those skilled in the-art from the foregoing description. Such modifications are intended to fall within the scope of the appended claims.

Various references are cited herein, the disclosures of which are incorporated by reference herein in their entirety.

What is claimed is:

1. A cosmetic composition comprising a cosmetic carrier and a plant extracellular matrix extract in an amount corresponding to a concentration of not less than about 0.1% by volume of said plant extracellular matrix extract in the composition, wherein said plant extracellular matrix comprises a glycoprotein in substantially native conformation, and a carbohydrate polymer in substantially native conformation.

2. The composition of claim 1 wherein the plant extracellular matrix extract is derived from a plant selected from the group consisting of kelp, Kudzu, maize, carrot, tomato, tobacco, bean, soybean, sugar beet, potato, melon and petunia.

3. The composition of claim 1 wherein the plant extracellular matrix extract is derived from primary or secondary plant cell wall.

4. The composition of claim 1 wherein the glycoprotein is selected from the group consisting of a hydroxyproline-rich protein, a repetitive proline-rich protein, a lectin and mixtures thereof.

5. The composition of claim 1 wherein the carbohydrate polymer is selected form the group consisting of pectin, xyloglycan, arabinoxylan, glycan, callose, lignin and mixtures thereof.

6. The composition of claim 1 wherein the glycoprotein is selected from the group consisting of a hydroxyproline-rich protein, a repetitive proline-rich protein, a lectin and mixtures thereof; and wherein the carbohydrate polymer is selected from the group consisting of pectin, xyloglycan, arabinoglycan, glucan, callose and lignin and mixtures thereof.

7. The composition of claim 1 wherein the cosmetic carrier is selected from the group consisting of a cream, an oil-in-water emulsion, a lotion and a gel.

8. The composition of claim 1 comprising plant extracellular matrix extract at a concentration of at least about 0.1%, by volume, of the cosmetic composition.

9. The composition of claim 1, further comprising an arabinogalactan protein in substantially native conformation.

10. A plant extracellular matrix extract comprising a glycoprotein in substantially native conformation, a carbohydrate polymer in substantially native conformation and an arabinogalactan protein in substantially native conformation.

11. The composition of claim 10 wherein the glycoprotein is selected from the group consisting of a hydroxyproline-rich protein, a repetitive proline-rich protein, a lectin and mixtures thereof.

12. The composition of claim 10 wherein the carbohydrate polymer is selected from the group consisting of pectin, xyloglucan, arabinoxylan, glucan, callose, lignin and mixtures thereof.

13. The composition of claim 10 wherein the extracellular matrix composition is derived from a plant selected from the group consisting of kelp, Kudzu, maize, carrot, tomato, tobacco, bean, soybean, sugar beet, potato, melon and petunia.

14. The composition of claim 10 wherein the matrix extract is derived from primary or secondary plant cell wall.

\* \* \* \* \*